United States Patent
Mizori et al.

(10) Patent No.: US 7,157,587 B2
(45) Date of Patent: Jan. 2, 2007

(54) IMIDE-EXTENDED LIQUID BISMALEIMIDE RESIN

(75) Inventors: Farhad G. Mizori, Lamesa, CA (US); Stephen M. Dershem, San Diego, CA (US)

(73) Assignee: Designer Molecules, Inc., San Diego, CA (US)

( * ) Notice: Subject to any disclaimer, the term of this patent is extended or adjusted under 35 U.S.C. 154(b) by 414 days.

(21) Appl. No.: 10/836,367

(22) Filed: Apr. 30, 2004

(65) Prior Publication Data

US 2004/0225059 A1    Nov. 11, 2004

Related U.S. Application Data

(60) Provisional application No. 60/468,017, filed on May 5, 2003.

(51) Int. Cl.
*C07D 403/14*    (2006.01)
*C08F 222/40*    (2006.01)

(52) U.S. Cl. .................... 548/461; 524/548; 428/473.5
(58) Field of Classification Search ................ 548/461; 524/548; 428/473.5
See application file for complete search history.

(56) References Cited

U.S. PATENT DOCUMENTS 6,034,194 A * 3/2000 Dershem et al. ............ 526/262

* cited by examiner

*Primary Examiner*—Fiona T. Powers
(74) *Attorney, Agent, or Firm*—Kevin J. Forrestal

(57) ABSTRACT

The invention is based on the discovery that a remarkable improvement in the performance of bismaleimide thermosets can be achieved through the incorporation of an imide-extended liquid bismaleimide monomer. This imide-extended liquid bismaleimide monomer is readily prepared by the condensation of an appropriate dianhydride with two equivalents of an appropriate diamine to give an amine terminated compound. This compound is then condensed with an excess of maleic anhydride to yield an imide-extended liquid bismaleimide monomer.

16 Claims, 1 Drawing Sheet

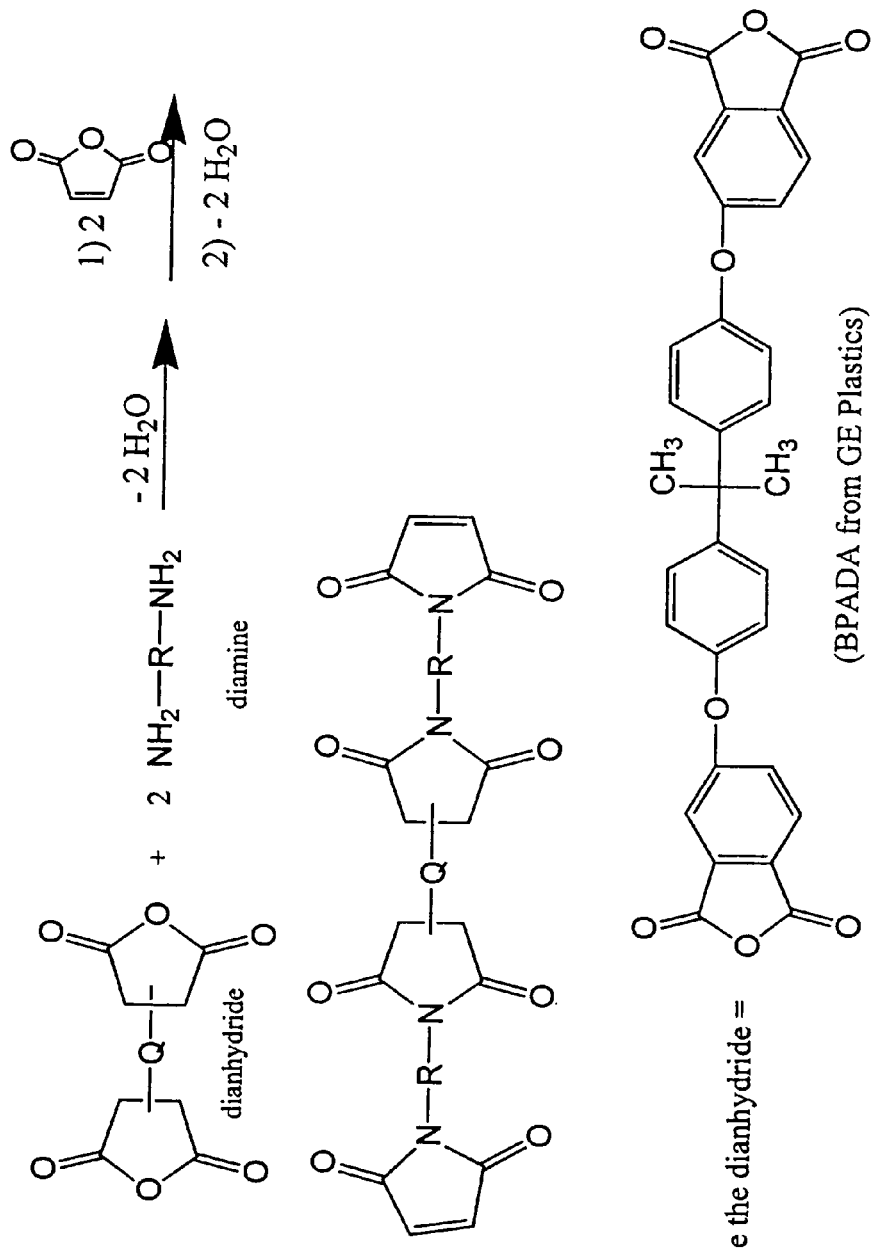

IMIDE-EXTENDED LIQUID BISMALEIMIDE RESIN

RELATED APPLICATION DATA

This application claims priority to Application Ser. No. 60/468,017, filed May 5, 2003, the entire contents of which are incorporated herein by reference.

FIELD OF THE INVENTION

The present invention relates to thermosetting adhesive compositions, methods of preparation and uses therefor. In particular, the present invention relates to thermosetting compounds and compositions containing an imide-extended liquid bismaleimide resin.

BACKGROUND OF THE INVENTION

Adhesive compositions, particularly conductive adhesives, are used for a variety of purposes in the fabrication and assembly of semiconductor packages and microelectronic devices. The more prominent uses include bonding of electronic elements such as integrated circuit chips to lead frames or other substrates, and bonding of circuit packages or assemblies to printed wire boards. Adhesives useful for electronic packaging applications typically exhibit properties such as good mechanical strength, curing properties that do not affect the component or the carrier, and thixotropic properties compatible with application to microelectronic and semiconductor components.

The bismaleimides represent one useful class of thermoset compounds that have been used in the microelectronic packaging industry. Bismaleimides are curable, meaning that they are capable of polymerization to yield cross-linked resins. In addition, bismaleimides may be homocured in the presence of free radicals or photoinitiators, or combined with other free-radical curing monomers (e.g., acrylates, methacrylates, syrenics, vinyl ethers, vinyl esters, allyl monomers, olefins, and the like). They may also be cured in the presence of comonomers via, Diels-Alder, -ene, and Michael addition mechanisms.

Commercially available bismaleimide thermoset compositions are noted for their high modulus, and excellent resistance to thermal degradation. However, these thermoset compositions are also well known for brittleness. The utility of the bismaleimide class of thermosets could be vastly improved if less brittle formulations could be achieved that retain the desirable thermal and elastic properties.

SUMMARY OF THE INVENTION

The present invention is based on the discovery that a remarkable improvement in the performance of bismaleimide thermosets can be achieved through the incorporation of an imide-extended liquid bismaleimide monomer. This imide-extended liquid bismaleimide monomer is readily prepared by the condensation of an appropriate dianhydride with two equivalents of an appropriate diamine to give an amine terminated compound. This compound is then condensed with an excess of maleic anhydride to yield an imide-extended liquid bismaleimide monomer.

When incorporated into a thermoset composition, the imide-linked maleimide monomer described herein reduces brittleness and increases toughness in the composition, while not sacrificing thermal stability. The imide functional group is one of the most thermally stable groups known. Thus, the present invention provides a maleimide functionalized thermoset composition without thermally labile linkages, thereby providing superior thermal stability when used as a toughener.

In one embodiment of the invention, there is provided a liquid imide-extended bismaleimide monomer having the structure:

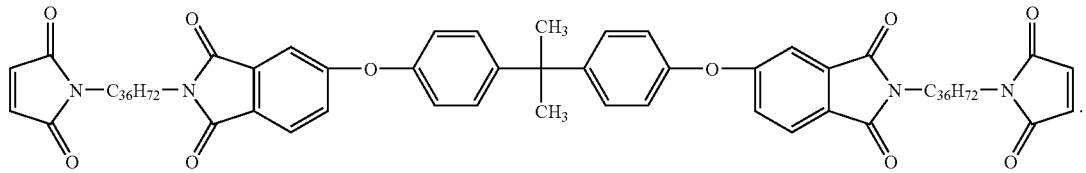

In another embodiment, there is provided an adhesive composition including a liquid imide-extended bismaleimide monomer having the structure set forth above; at least one co-monomer selected from the group consisting of acrylates, methacrylates, maleimides, vinyl ethers, vinyl esters, styrenic compounds, and allyl functional compounds; and at least one curing initiator.

In another embodiment of the invention, there is provided a die-attach adhesive composition including 2 weight percent to about 98 weight percent (wt %) of the liquid imide-extended bismaleimide monomer having the structure set forth above based on total weight of the composition; 10 wt % to about 90 wt % of at least one co-monomer selected from the group consisting of acrylates, methacrylates, maleimides, vinyl ethers, vinyl esters, styrenic compounds, and allyl functional compounds, based on total weight of the composition; 0 to about 90 wt % of a conductive filler; 0.1 wt % to about 5 wt % of at least one curing initiator, based on total weight of the composition; and 0.1 wt % to about 4 wt %, of at least one coupling agent, based on total weight of the composition.

In still another embodiment, there is provided a method for producing a liquid imide-extended bismaleimide monomer. Such a method can be performed, for example, by contacting 4,4'-bisphenol A dianhydride (BPADA) with a diamine under conditions suitable to form an imide having terminal amino moieties; and contacting the terminal amino moieties with maleic anhydride under conditions suitable to form a maleimide, thereby producing a liquid imide-extended bismaleimide monomer.

BRIEF DESCRIPTION OF THE DRAWINGS

FIG. 1 illustrates the preparation of a liquid imide-extended bismaleimide monomer of this invention.

DETAILED DESCRIPTION OF THE INVENTION

The present invention is based on the discovery that a remarkable improvement in the performance of bismaleimide thermosets can be achieved through the incorporation of an imide-extended liquid bismaleimide monomer. In one embodiment, there is provided a liquid imide-extended bismaleimide monomer having the structure (I):

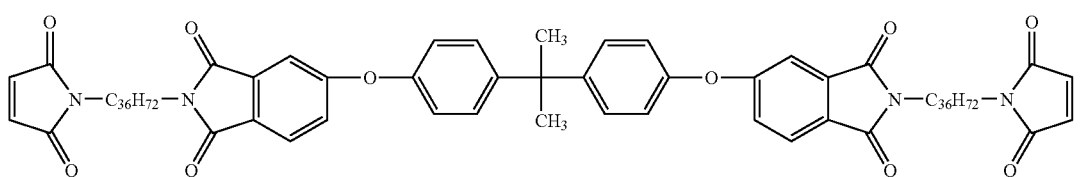

In the structure set forth above, the $C_{36}H_{72}$ aliphatic moiety is derived from the hydrogenated dimer diamine Versamine 552 (Cognis), and can be represented by the following structure:

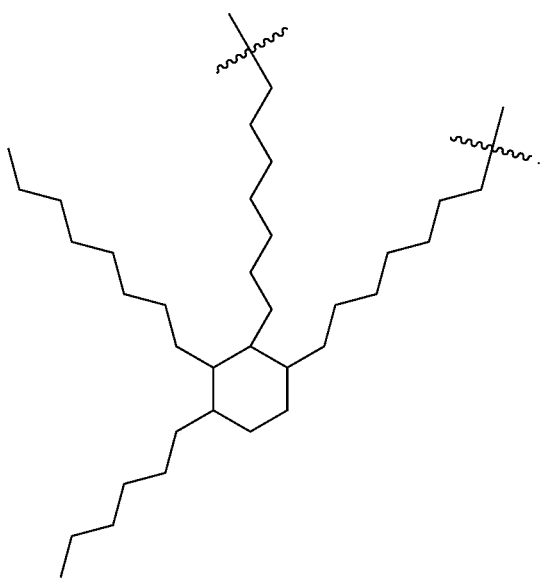

Referring to FIG. 1, compound (I) is readily prepared by a two-step, single-pot synthesis. The first step involves the condensation of a dianhydride (BPADA from General Electric) with dimer diamine (Versamine 552 from Cognis Corporation) to form an amine-terminated polyimide. The diamine should be present in at least a slight excess of that necessary to form the imide-linked diamine intermediate.

The second step of the reaction involves the condensation of the remaining amine residues with a slight excess of maleic anhydride to form the maleimide moieties. This second step can be accomplished employing techniques well known to those of skill in the art. The most straightforward preparation of maleimides entails formation of the maleamic acid via reaction of the primary amine with maleic anhydride, followed by dehydrative closure of the maleamic acid with acetic anhydride. A major complication is that some or all of the closure is not to the maleimide, but to the isomaleimide. Essentially the isomaleimide is the dominant or even exclusive kinetic product, whereas the desired maleimide is the thermodynamic product. Conversion of the isomaleimide to the maleimide is effectively the slow step and, particularly in the case of aliphatic amines, may require forcing conditions which can lower the yield. Of course, a variety of other approaches can also be employed.

For example, dicyclohexylcarbodiimide (DCC) closes maleamic acids much more readily than does acetic anhydride. With DCC, the product is exclusively isomaleimide. However, in the presence of suitable isomerizing agents, such as 1-HOBt hydroxybenzotriazole (HOBt), the product is solely the maleimide. The function of the could be to allow the closure to proceed via the HOBt ester of the maleamic acid (formed via the agency of DCC) which presumably closes preferentially to the maleimide. Likely, isomerizing agents such as HOBt add to the isoimide to yield the amic acid ester. If this exhibits any tendency whatsoever to close to the imide, much less a strong bias for doing so, a route for interconverting isoimide and imide is thereby established and the thermodynamic product, imide, should ultimately prevail. Thus if the initial closure of ester formed in the DCC reaction yields any isoimide, or if any isoimide is produced by direct closure of the acid, the situation will be subsequently "corrected" via conversion of the isoimide to the imide by the action of the active ester alcohol as an isomerizing agent.

An alternative method for affecting the cyclodehydration of maleamic acids is set forth in U.S. Pat. No. 5,973,166, the entire contents of which are incorporate dherein by reference. This method utilizes amine salts that can be successfully used to replace the polar, aprotic solvents that have been used for the cyclodehydration of maleamic acids. The use of these salts provides competitive reaction times and product yields relative to results obtained with polar, aprotic solvents. These salts have the advantage of having no vapor pressure and, therefore, have no possibility to co-distill with the water produced by the cyclodehydration reaction. Furthermore, such salts can be tailored to have desirable solubility characteristics (i.e., soluble in the refluxing azeotropic solvent, but insoluble at room temperature) that permit their easy removal from the reaction product. Such salts are not destroyed during the cyclodehydration reaction and, therefore, can be efficiently recycled again and again.

The liquid imide-extended bismaleimide monomer of the invention may be used independently in adhesive compositions, or may be combined with other adhesive compounds and resins. In one embodiment, the bismaleimide monomer of the invention may be used as the sole thermoset monomer of the adhesive composition. In another embodiment, the bismaleimide monomer of the invention may be combined the bismaleimide with other thermoset monomers to make a fully formulated adhesive. Thus, in one embodiment, there is provided an adhesive composition including the liquid imide-extended bismaleimide monomer of structure (I), at least one co-monomer selected from the group consisting of acrylates, methacrylates, maleimides, vinyl ethers, vinyl esters, styrenic compounds, allyl functional compounds, and the like; and at least one curing initiator.

In some embodiments, the liquid imide-extended bismaleimide monomer is present in the composition from 2 weight percent to about 98 weight percent (wt %) based on total weight of the composition. In other embodiments, the at least one co-monomer typically is present in the composition from 10 wt % to about 90 wt % based on total weight of the composition.

The at least one curing initiator is typically present in the composition from 0.1 wt % to about 5 wt % based on total weight of the composition, and is typically a free-radical initiator. As used herein, the term "free radical initiator" refers to any chemical species which, upon exposure to sufficient energy (e.g., light, heat, or the like), decomposes into two parts which are uncharged, but which each possess at least one unpaired electron. Preferred free radical initiators contemplated for use in the practice of the present invention are compounds which decompose (i.e., have a half life in the range of 0.01 to about 10 hours) at temperatures in the range of about 70° C. up to 180° C. Exemplary free radical initiators contemplated for use in the practice of the present invention include peroxides (e.g., dicumyl peroxide, dibenzoyl peroxide, 2-butanone peroxide, tert-butyl perbenzoate, di-tert-butyl peroxide, 2,5-bis(tert-butylperoxy)-2,5-dimethylhexane, bis(tert-butyl peroxyisopropyl)benzene, and tert-butyl hydroperoxide), azo compounds (e.g., 2,2'-azobis(2-methyl-propanenitrile), 2,2'-azobis(2-methylbutanenitrile), and 1,1'-azobis(cyclohexanecarbonitrile)), and the like.

The term "free radical initiator" also includes photoinitiators. For example, for invention adhesive compositions that contain a photoinitiator, the curing process can be initiated by UV radiation. In one embodiment, the photoinitiator is present at a concentration of 0.1 wt % to 5 wt % based on the total weight of the organic compounds in the composition (excluding any filler). In a one embodiment, the photoinitiator comprises 0.1 wt % to 3.0 wt %, based on the total weight of the organic compounds in the composition. Photoinitiators include benzoin derivatives, benzilketals, α,α-dialkoxyacetophenones, α-hydroxyalkylphenones, α-aminoalkylphenones, acylphosphine oxides, titanocene compounds, combinations of benzophenones and amines or Michler's ketone, and the like.

In another embodiment of the invention, there are provided die-attach pastes including 2 weight percent to about 98 weight percent (wt %) of the liquid imide-extended bismaleimide monomer of structure (I), based on total weight of the composition; 10 wt % to about 90 wt % of at least one co-monomer selected from the group consisting of acrylates, methacrylates, maleimides, vinyl ethers, vinyl esters, styrenic compounds, and allyl functional compounds, and the like, based on total weight of the composition; 0 to about 90 wt % of a conductive filler; 0.1 wt % to about 5 wt % of at least one curing initiator, based on total weight of the composition; and 0.1 wt % to about 4 wt %, of at least one coupling agent, based on total weight of the composition.

Fillers contemplated for use in the practice of the present invention can be electrically conductive and/or thermally conductive, and/or fillers which act primarily to modify the rheology of the resulting composition. Examples of suitable electrically conductive fillers which can be employed in the practice of the present invention include silver, nickel, copper, aluminum, palladium, gold, graphite, metal-coated graphite (e.g., silver-coated copper, nickel-coated graphite, copper-coated graphite, and the like), and the like. Examples of suitable thermally conductive fillers which can be employed in the practice of the present invention include graphite, aluminum nitride, silicon carbide, boron nitride, diamond dust, alumina, and the like. Compounds which act primarily to modify rheology include fumed silica, alumina, titania, and the like.

As used herein, the term "coupling agent" refers to chemical species that are capable of bonding to a mineral surface and which also contain polymerizably reactive functional group(s) so as to enable interaction with the adhesive composition. Coupling agents thus facilitate linkage of the die-attach paste to the substrate to which it is applied.

Exemplary coupling agents contemplated for use in the practice of the present invention include silicate esters, metal acrylate salts (e.g., aluminum methacrylate), titanates (e.g., titanium methacryloxyethylacetoacetate triisopropoxide), or compounds that contain a copolymerizable group and a chelating ligand (e.g., phosphine, mercaptan, acetoacetate, and the like). In some embodiments, the coupling agents contain both a co-polymerizable function (e.g., vinyl moiety, acrylate moiety, methacrylate moiety, and the like), as well as a silicate ester function. The silicate ester portion of the coupling agent is capable of condensing with metal hydroxides present on the mineral surface of substrate, while the co-polymerizable function is capable of co-polymerizing with the other reactive components of invention die-attach paste. In certain embodiments coupling agents contemplated for use in the practice of the invention are oligomeric silicate coupling agents such as poly(methoxyvinylsiloxane).

In some embodiments, both photoinitiation and thermal initiation may be desirable. For example, curing of a photoinitiator-containing adhesive can be started by UV irradiation, and in a later processing step, curing can be completed by the application of heat to accomplish a free-radical cure. Both UV and thermal initiators may therefore be added to the adhesive composition.

In general, these compositions will cure within a temperature range of 80–220° C., and curing will be effected within a length of time of less than 1 minute to 60 minutes. As will be understood by those skilled in the art, the time and temperature curing profile for each adhesive composition will vary, and different compositions can be designed to provide the curing profile that will be suited to the particular industrial manufacturing process.

In certain embodiments, the adhesive compositions may contain compounds that lend additional flexibility and toughness to the resultant cured adhesive. Such compounds may be any thermoset or thermoplastic material having a Tg of 50° C. or less, and typically will be a polymeric material characterized by free rotation about the chemical bonds, the presence of ether groups, and the absence of ring structures. Suitable such modifiers include polyacrylates, poly(butadiene), polyTHF (polymerized tetrahydrofuran), CTBN (carboxy-terminated butadiene-acrylonitrile) rubber, and polypropylene glycol. When present, toughening compounds may be in an amount up to about 15 percent by weight of the maleimide and other monofunctional vinyl compound.

Inhibitors for free-radial cure may also be added to the adhesive compositions and die-attach pastes described herein to extend the useful shelf life of compositions containing the imide-extended maleimides. Examples of these inhibitors include hindered phenols such as 2,6-di-tert-butyl-4-methylphenol; 2,6-di-tert-butyl-4-methoxyphenol; tert-butyl hydroquinone; tetrakis(methylene(3,5-di-tert-butyl-4-hydroxyhydocinnamate))benzene; 2,2'-methylenebis(6-tertbutyl-p-cresol); and 1,3,5-trimethyl-2,4,6-tris(3',5'-di-tert-butyl-4-hydroxybenzyl)benzene. Other useful hydrogen-donating antioxidants include derivatives of p-phenylenediamine and diphenylamine. It is also well know in the art that hydrogen-donating antioxidants may be synergistically combined with quinones, and metal deactivators to make a very efficient inhibitor package. Examples of suitable quinones include benzoquinone, 2-tert butyl-1,4-benzoquinone; 2-phenyl-1,4-benzoquinone; naphthoquinone, and 2,5-dichloro-1,4-benzoquinone. Examples of metal deactivators include N,N'-bis(3,5-di-tert-butyl-4-hydroxyhydrocinnamoyl)hydrazine; oxalyl bis(benzylidenehydrazide); and N-phenyl-N'-(4-toluenesulfonyl)-p-phenylenediamine. Nitroxyl radical compounds such as TEMPO (2,2,6,6-tetramethyl-1-piperidnyloxy, free radical) are also effective as inhibitors at low concentrations. The total amount of antioxidant plus synergists typically falls in the range of 100 to 2000 ppm relative to the weight of total base resin. Other additives, such as adhesion promoters, in types and amounts known in the art, may also be added.

These compositions will perform within the commercially acceptable range for die attach adhesives. Commerically acceptable values for die shear for the adhesives on a 80×80 mil² silicon die are in the range of greater than or equal to 1 kg at room temperature, and greater than or equal to 0.5 kg at 240° C. Acceptable values for warpage for a 500×500 mil² die are in the range of less than or equal to 70 Nm at room temperature.

The coefficient of thermal expansion (CTE) is the change in dimension per unit change in temperature for a given material. Different materials will have different rates of expansion. If the CTE is very different for elements attached together, thermal cycling can cause the attached elements to bend, crack, or delaminate. In a typical semiconductor assembly, the CTE of the chip is in the range of 2 or 3 ppm/° C.; for organic circuit board substrate, the CTE is greater than 30 ppm/° C.; therefore, the CTE of the adhesive is best between that of the substrate and die.

When a polymer is subjected to the application of heat, it will move through a transition region between a hard, glassy state to a soft, rubbery state. This region is known as the glass transition region or Tg. If a graph of expansion of the polymer versus temperature is plotted, the glass transition region is the intersection between the lower temperature/glassy region coefficient of thermal expansion and the higher temperature/rubbery region coefficient of thermal expansion. Above this region, the rate of expansion increases significantly. Consequently, it is preferred that the glass transition of the polymer be higher-than-normal operating temperatures experienced during the application. Alternatively, if the modulus of the polymer bonding material is low enough then the adhesive can adsorb most of the stresses induced by the thermal expansion mismatches between the chip and substrate.

In yet another embodiment of the invention, there are provided assemblies of components adhered together employing the above-described adhesive compositions and/or die attach pastes. Thus, for example, assemblies comprising a first article permanently adhered to a second article by a cured aliquot of the above-described adhesive composition are provided. Articles contemplated for assembly employing invention compositions include memory devices, ASIC devices, microprocessors, flash memory devices, and the like.

Also contemplated are assemblies comprising a microelectronic device permanently adhered to a substrate by a cured aliquot of the above-described die attach paste. Microelectronic devices contemplated for use with invention die attach pastes include copper lead frames, Alloy 42 lead frames, silicon dice, gallium arsenide dice, germanium dice, and the like.

In accordance with still another embodiment of the present invention, there are provided methods for adhesively attaching two component parts to produce the above-described assemblies. Thus, for example, a first article can be adhesively attached to a second article, employing a method including:
(a) applying the above-described adhesive composition to the first article,
(b) bringing the first and second article into intimate contact to form an assembly wherein the first article and the second article are separated only by the adhesive composition applied in (a), and thereafter,
(c) subjecting the assembly to conditions suitable to cure the adhesive composition.

Similarly, a microelectronic device can be adhesively attached to a substrate, employing a method comprising:
(a) applying the above-described die attach paste to the substrate and/or the microelectronic device,
(b) bringing the substrate and the device into intimate contact to form an assembly wherein the substrate and the device are separated only by the die attach composition applied in (a), and thereafter,
(c) subjecting the assembly to conditions suitable to cure the die attach composition.

Conditions suitable to cure invention die attach pastes include subjecting the above-described assembly to a temperature of less than about 200° C. for about 0.5 up to 2 minutes. This rapid, short duration heating can be accomplished in a variety of ways, e.g., with an in-line heated rail, a belt furnace, or the like.

In still another embodiment of the invention, there is provided a method for producing a liquid imide-extended bismaleimide monomer. Such a method can be performed, for example, by contacting 4,4'-bisphenol A dianhydride (BPADA) with a diamine under conditions suitable to form an imide having terminal amino moieties; and contacting the terminal amino moieties with maleic anhydride, thereby producing a liquid imide-extended bismaleimide monomer.

The following examples are intended only to illustrate the present invention and should in no way be construed as limiting the subject invention.

EXAMPLES

Example 1

Synthesis of Liquid Imide-Extended Bismaleimide Monomer

Toluene (350 ml) was added to a one liter round bottom flask equipped with a Teflon coated stir bar. Triethylamine, 50 g (~0.50 mole) was added to the flask followed by the slow addition of 50 g (0.52 mole) of anhydrous methanesulphonic acid. The mixture was allowed to stir at room temperature approximately 10 minutes, followed by the addition of 90 g (0.17 mole) of Versamine 552 (dimer diamine, Cognis Corporation). To the mixture was added 41 g (0.08 mole) of BPADA (4,4'-bisphenol-A dianhydride, GE Plastics). A Dean-Stark trap and condenser were attached to the flask, and the mixture was heated to reflux. After approximately two hours the expected amount of water was collected corresponding to the complete conversion to the amine terminated diimide. The mixture was allowed to cool down to below 40° C., and 22 g (0.23 mole, ~20% excess) of crushed maleic anhydride was added to the flask, followed by the addition of an extra 10 g of anhydrous methanesulphonic acid. The mixture was again slowly heated to reflux. Approximately 18 hours of reflux were required to collect the expected amount of water in the Dean-Stark trap. After cooling down to room temperature an extra 200 ml of toluene was added to the flask; the stirring was stopped at this point and the mixture was allowed to separate. The upper (toluene solution) fraction was carefully decanted into a 2 liter Erlenmeyer flask. The salt was washed with toluene (2×500 ml) the rinses were also decanted and combined. The amber solution was allowed to settle overnight to allow sufficient time for more salt and acid to separate from the combined toluene solution. The solution was then filtered through a glass-fritted funnel tightly packed with 65 g of silica gel. Following filtration the silica gel was washed with an extra 100 ml of toluene. The toluene was removed under reduced pressure to provide a crude yield of 120 g (~85% crude yield) of a dark amber viscous fluid. Thermogravimetric analysis of this product (10° C./min. in air) indicated that there was less than one-half percent weight loss by 300° C. and an onset for decomposition at 454° C. Compound of structure (I) is then isolated by routine analytical techniques, well-known to those skilled in the art.

Example 2

Tensile Adhesion Test Results for the Liquid Imide-Extended Bismaleimide

Tensile adhesion testing was done on some of the product from Example 1 The only component added to the test resin was 2% by weight of dicumyl peroxide initiator. The catalyzed resin mix was then used to affix aluminum studs to copper slugs. The aluminum posts had a contact head diameter of 290 mils. The copper slugs had dimensions of 1000×400×150 mils. Ten of these test assemblies were constructed for each of the catalyzed resin mixtures. The parts were cured for thirty minutes in an oven at 200° C. The Parts were then allowed to cool to room temperature and the adhesive strength was determined using a Sebastian III tensile tester. A control composition was also run along side the test mixtures. The control mix used was the bismaleimide derived from the dimer diamine (i.e. Versamine 552) also catalyzed with 2% dicumyl peroxide.

TABLE 1

Tensile Adhesion Test Results

| Part | Stud Pull Value (pounds force) | |
| --- | --- | --- |
|  | Example 1 | Control |
| 1 | 66 | 23 |
| 2 | 54 | 16 |
| 3 | 57 | 15 |
| 4 | 75 | 12 |
| 5 | 47 | 19 |
| 6 | 71 | 9 |
| 7 | 52 | 22 |
| 8 | 70 | 18 |
| 9 | 63 | 8 |
| 10 | 77 | 6 |
| Average | 63 | 15 |
| $F_{n-1}$ | 10 | 6 |

The liquid bismaleimide rubber from Example 1 had more than four times the average adhesion of the corresponding control. While not wishing to be bound by theory, it is believed that the improvement seen here is a direct result of the reduced cross-link density and/or reduced cure shrinkage of the invention composition versus the BMI derived solely from the dimer diamine.

While the invention has been described in detail with respect to these specific examples, it is understood that modifications and variations are within the spirit and scope of that which is described and claimed.

What is claimed is:

1. A liquid imide-extended bismaleimide monomer having the structure:

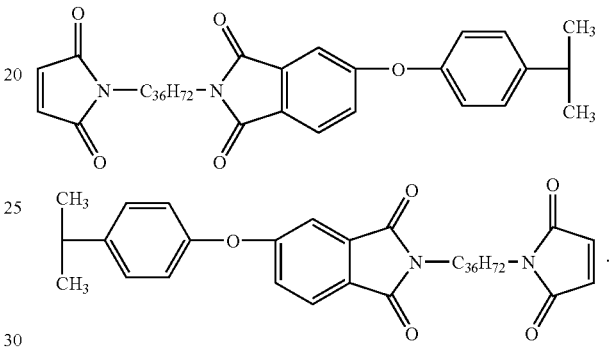

2. An adhesive composition comprising:
    a) the liquid imide-extended bismaleimide monomer of claim 1;
    b) at least one co-monomer selected from the group consisting of acrylates, methacrylates, maleimides, vinyl ethers, vinyl esters, styrenic compounds, and allyl functional compounds; and
    c) at least one curing initiator.

3. The adhesive composition of claim 2, wherein the liquid imide-extended bismaleimide monomer comprises 2 weight percent to about 98 weight percent (wt %) based on total weight of the composition.

4. The adhesive composition of claim 2, wherein the at least one co-monomer comprises 10 wt % to about 90 wt % based on total weight of the composition.

5. The adhesive composition of claim 2, wherein the at least one curing initiator comprises 0.1 wt % to about 5 wt % based on total weight of the composition.

6. The adhesive composition of claim 2, wherein the curing initiator comprises a free-radical initiator or a photoinitiator.

7. A die-attach paste comprising:
    a) 2 weight percent to about 98 weight percent (wt %) of the liquid imide-extended bismaleimide monomer of claim 1, based on total weight of the composition.
    b) 10 wt % to about 90 wt % of at least one co-monomer selected from the group consisting of acrylates, methacrylates, maleimides, vinyl ethers, vinyl esters, styrenic compounds, and allyl functional compounds, based on total weight of the composition;
    c) 0 to about 90 wt % of a conductive filler;
    d) 0.1 wt % to about 5 wt % of at least one curing initiator, based on total weight of the composition;
    e) 0.1 wt % to about 4 wt %, of at least one coupling agent, based on total weight of the composition.

8. The die-attach paste of claim 7, wherein the coupling agent is a silicate ester, a metal acrylate salt, or a titanate.

9. The die-attach paste of claim 7, wherein the conductive filler is electrically conductive.

10. The die-attach paste of claim 7, wherein the at least one curing initiator is a peroxide.

11. A method for producing a liquid imide-extended bismaleimide monomer comprising:

contacting 4,4'-bisphenol A dianhydride (BPADA) with a diamine under conditions suitable to form an imide having terminal amino moieties; and contacting the terminal amino moieties with maleic anhydride under conditions suitable to form a maleimide, thereby producing a liquid imide-extended bismaleimide monomer.

12. A liquid imide-extended bismaleimide monomer prepared according to the method of claim 11.

13. An assembly comprising a first article permanently adhered to a second article by a cured aliquot of the die-attach paste of claim 7.

14. The assembly of claim 13, wherein said first and said second articles comprise memory devices, ASIC devices, microprocessors, or flash memory devices.

15. A method for adhesively attaching a first article to a second article, comprising:

(a) applying an aliquot of the adhesive composition of claim 2 to the first article, (b) bringing the first and second article into intimate contact to form an assembly wherein the first article and the second article are separated only by the adhesive composition applied in (a), and thereafter, (c) subjecting the assembly to conditions suitable to cure the adhesive composition.

16. A method for adhesively attaching a microelectronic device to a substrate comprising:

(a) applying the die attach paste of claim 7 to the substrate and/or the microelectronic device, (b) bringing the substrate and the device into intimate contact to form an assembly wherein the substrate and the device are separated only by the die-attach paste applied in (a), and thereafter, (c) subjecting the assembly to conditions suitable to cure the die attach paste.

* * * * *